US00PP35269P2

(12) United States Plant Patent
Olesen et al.

(10) Patent No.: US PP35,269 P2
(45) Date of Patent: Jul. 18, 2023

(54) ***CLEMATIS* PLANT NAMED 'EVIPO115'**

(50) Latin Name: *Clematis viticella*
Varietal Denomination: Evipo115

(71) Applicants: Mogens Nyegaard Olesen, Fredensborg (DK); Raymond J Evison, Guernsey (GB)

(72) Inventors: Mogens Nyegaard Olesen, Fredensborg (DK); Raymond J Evison, Guernsey (GB)

(73) Assignee: POULSEN ROSER A/S & RAMOND J. EVISON LTD, Fredensborg (DK)

( * ) Notice: Subject to any disclaimer, the term of this patent is extended or adjusted under 35 U.S.C. 154(b) by 0 days.

(21) Appl. No.: 17/803,629

(22) Filed: Sep. 13, 2022

(30) Foreign Application Priority Data

Sep. 24, 2021 (QZ) ..... PBR 2021/2369

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./228
See application file for complete search history.

(56) References Cited

PUBLICATIONS https://www.rhs.org.uk/plants/plants-blogs/plants/june-2019/clematis-elodi-evipo115. Retrieved from the Internet on Dec. 13, 2022.*

* cited by examiner

*Primary Examiner* — Susan McCormick Ewoldt

(57) ABSTRACT

A new *Clematis* plant with a compact growth habit, profuse, purple flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification:
Genus: *Clematis.*
Species: *viticella.*
Variety denomination: 'Evipo115'.

This application claims priority to Plant Breeder's Rights Application Number 2021/2369, which was filed at the Community Plant Variety Rights Office in the European Union on Sep. 24, 2021, the contents of which are hereby incorporated by reference for all purposes.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2007 and the resulting seeds were planted the following winter in a controlled environment in Guernsey, Channel Islands, United Kingdom. The new variety named 'Evipo115' originated as a single seedling from the stated cross.

The new *Clematis* plant may be distinguished from its female seed parent and male pollen parent by the following characteristics. The female seed parent grows to 60 cm in one season while the new variety grows only to 15 cm in one season. The male seed parent has yellow anthers while the new variety has Greyed-Purple Group N186A anthers.

The objective of the hybridization of this *Clematis* plant was to create a new and distinct variety for nursery culture with unique qualities such as:

1. Uniform and abundant purple flowers;
2. Vigorous and compact growth, making the variety suitable for container culture; and
3. Improved disease resistance.

This combination of qualities was lacking in *Clematis* plants that were in commercial cultivation and the qualities have been substantially achieved in the new variety.

'Evipo115' was selected by Mogens N. Olesen and Raymond J. Evison in their *Clematis* development program in the Channel Islands, United Kingdom in 2008. Asexual reproduction of 'Evipo115' by means of vegetative cuttings and traditional layering was first performed by Mogens N. Olesen and Raymond J. Evison in the nursery during the summer of 2008. This initial and subsequent asexual propagations have demonstrated that the characteristics of 'Evipo115' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo115'.

Specifically illustrated in FIG. 1 of the drawings are open flowers viewed from above and underneath, and the tepals detached revealing reproductive flower parts.

DETAILED DESCRIPTION OF THE VARIETY

Figure 1:
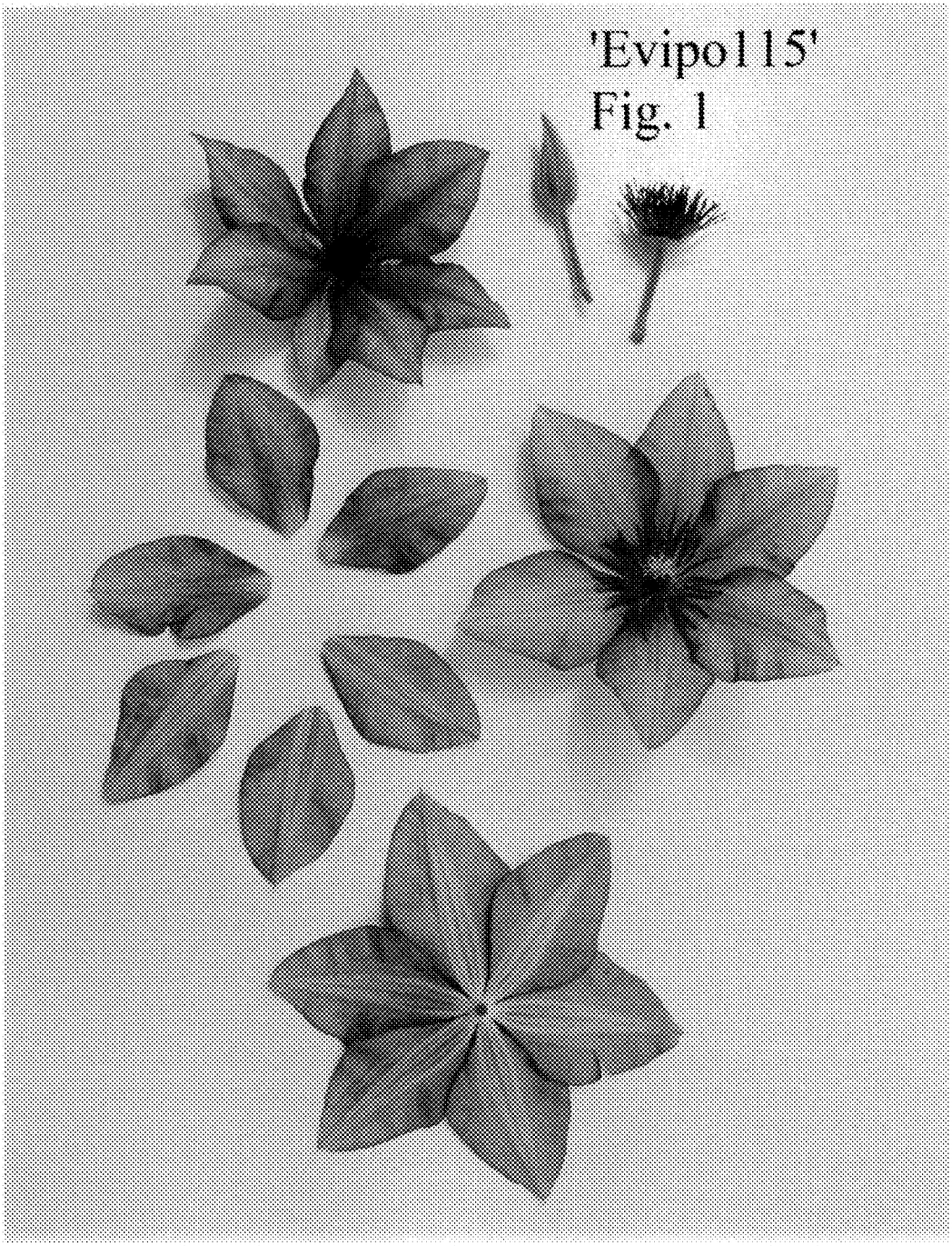
Figure 2:
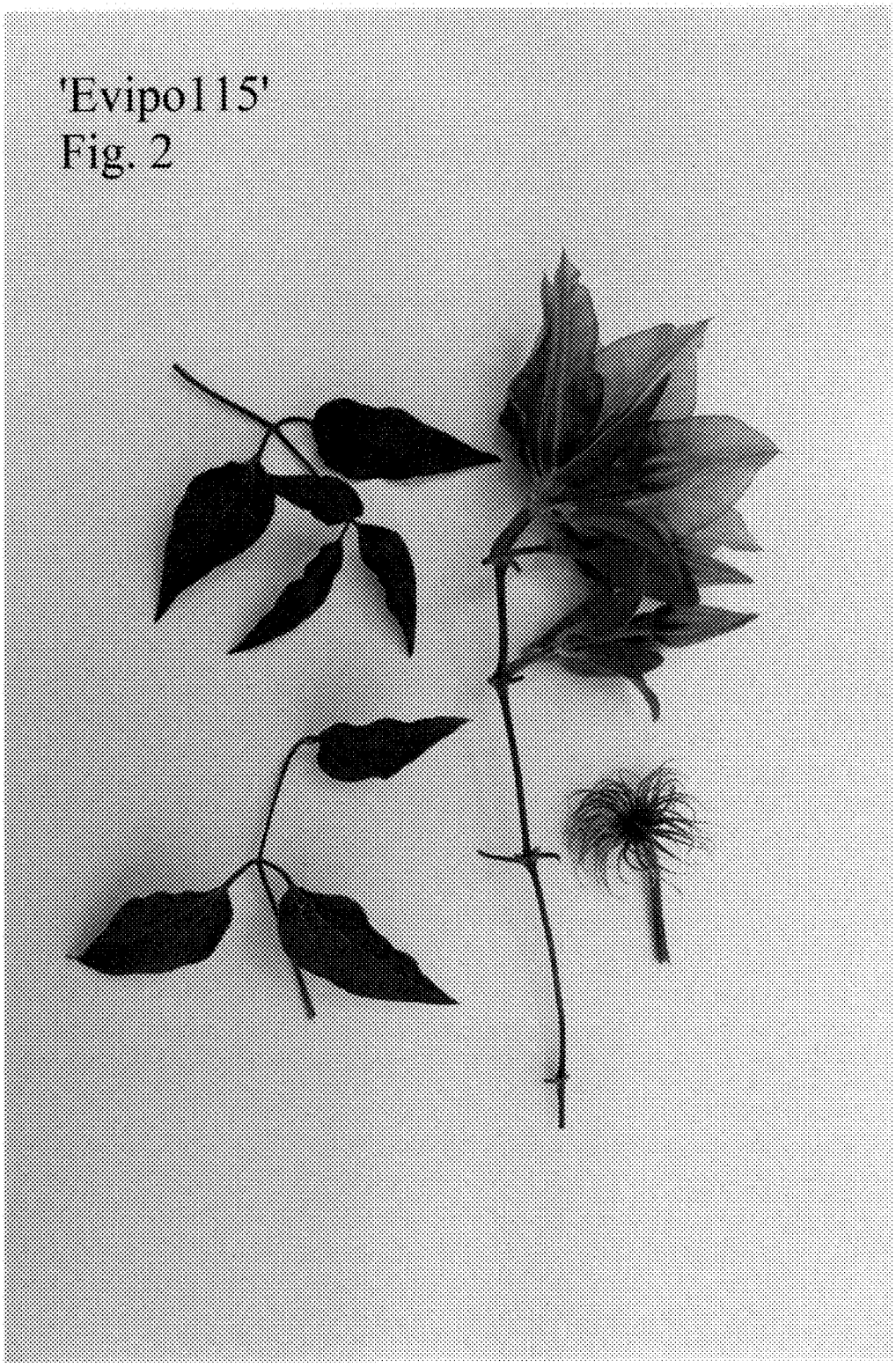
FIG. 2 shows leaves, a stem bearing clusters of open flowers and flower buds. Illustrated plants are 2 years of age.

The following is a detailed description of 'Evipo115', as observed in its growth throughout the flowering period in Odense. Observed plants were cultivated for a period of 24 months in 24 cm containers, outdoor. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *Clematis* variety 'Evipo051' described and illustrated in U.S. Plant Pat. No. 27,280 are compared to 'Evipo115'. The claimed plant has a tepal colour after opening, on the upper surface Violet Group 84C with marginal intonations of Purple Group 77A while the comparison variety has a tepal colour after opening, upper surface Red-Purple Group 62C with central bar and margins of Purple Group N77B. The comparison variety in one season attains 50 to 60 cm in growth height. The claimed plant is very compact growing to 15 cm in height.

FLOWER AND FLOWER BUD

Blooming habit: Continuous, flowering on new growth. The natural flowering period is generally from April to September.

Flower bud:
- *Size*.—Normally 31 mm in length. Bud diameter is 12 mm.
- *Bud form*.—Long campanulate, broad based.
- *Bud color*.—Greyed Group 201B with intonations of Purple Group 76A.
- *Texture*.—Pubescent.

Pedicel:
- *Surface texture*.—Smooth, and lightly pubescent.
- *Length*.—On average 23 mm in length with 2 mm diameter.
- *Color*.—Yellow-Green Group 146C with intonations of Greyed Purple Group 183C.
- *Strength*.—Moderately strong.

Receptacle:
- *Surface texture*.—Lightly pubescent.
- *Shape*.—Broad funnel.
- *Size*.—2 mm (h)×4 mm (w).
- *Color*.—Yellow-Green Group 146C.

Flower arrangement:
- *Location on vine*.—Flowers develop on both old and new growth at the terminal bud and axillary bud.
- *Borne*.—In clusters of 5 to 7 flowers per flowering branch.

Flower bloom:
- *Size*.—On average, flowers are 120 mm in diameter and 20 mm in depth.
- *Profile*.—Open flowers are flat.
- *Fragrance*.—None.
- *Lasting quality*.—Flowers normally remain up to 10 days on the plant.

Tepals:
- *General tonality*.—Purple Group 76B and Purple Group 77A. After flowers have been open 7 to 10 days, Purple Group 76B with marginal intonations of Purple Group 77A.
- *Tepal color*.—Upon opening, the upper surface is Purple Group N79C with other intonations of Purple Group 77D. The lower surface is Purple Group N79D. Central bar Greyed Green 197B. After opening, the upper surface is Violet Group 84C with marginal intonations of Purple Group 77A. The lower surface is Violet Group 85B and Purple Group 77A. The central bar is color Purple Group 76D.
- *Quantity*.—Normally 6 or 7 tepals.
- *Size*.—Tepals are about 70 mm in length by 38 mm wide.
- *Shape*.—Individual tepal shape is elliptic. The tepal apex is acuminate. The tepal base is acute.
- *Apex recurvature*.—Slightly recurved outward.
- *Tepal cross section*.—Flat.
- *Margins*.—Entire. Slight undulations of margin observed.
- *Persistence*.—Tepals drop off cleanly.

Reproductive organs:
- *Pollen*.—None observed.
- *Anthers*.—Size: 8 mm in length. Color: Greyed-Purple Group N186A. Quantity: On average, 65.
- *Filaments*.—Color: Purple-Violet Group N80C. Length: 8 mm.
- *Pistils*.—Quantity: On average, 25.
- *Stigmas*.—Superior in location relative to the length of the filaments and the height of the anthers.
- *Styles*.—Color: White Group 155A. Length: 14 mm.

Seed head characteristics:
- *Size*.—45 mm diameter. 20 mm in height.
- *Quantity*.—About 50 seeds produced per seed head.
- *Style appearance*.—Smooth, 20 mm in length.
- *Color*.—Yellow-Green Group 145A and Greyed-Yellow Group 162D.

PLANT

Plant form: Low growing, mounding, somewhat spreading.

Plant growth: Very compact.

Size: Seasons growth attains 15 cm in height. Average spread is 37 cm.

Stems:
- *Color*.—Juvenile stems are Yellow-Green Group 144A. Mature stems are Greyed-Orange Group 166A.
- *Internodes*.—On average, 45 to 65 mm between nodes.
- *Length*.—About 5 cm from the base of the plant to the flowering portion of the stem.
- *Diameter*.—About 3 mm.
- *Texture*.—Mature stems are ribbed. Pubescent.

Plant foliage:
- *Leaf characteristics*.—Deciduous.
- *Arrangement*.—Trifoliate. Compound leaf with 5 leaflets.
- *Leaf size*.—Compound leaves are about 120 mm (l)× 130 mm (w). Leaflets are about 48 mm (l)×24 mm (w).
- *Abundance*.—On average 2 leaves per 10 cm of stem.
- *Leaf color*.—Juvenile upper Yellow-Green Group 147A. Juvenile lower Yellow-Green Group 148D.

Mature upper Yellow-Green Group 147A. Mature lower Yellow-Green Group 148D.

*Stipules*.—Absent.

*Petioles*.—Size: Normally 35 mm in length by 1.5 mm diameter. Texture: Smooth. Color: Greyed-Orange Group 177A.

*Petioloule*.—Size: About 8 mm in length by 1.5 mm diameter. Texture: Pubescent. Color: Greyed-Orange Group 177A.

*Leaflet shape*.—Elliptic. The base is rounded, apex acute.

*Margin*.—Entire.

*Surface*.—The upper side is smooth, the lower side is smooth.

*Thickness*.—Moderate.

*Glossiness*.—Not glossy.

Disease resistance: Subject to any disease that normally attacks the species. However the variety is more tolerant to *Clematis* wilt, *Ascochyta clematidina*, than some *Clematis* known to the inventors.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *Clematis* plant named 'Evipo115', substantially as described and illustrated herein.

* * * * *

'Evipo115'

'Evipo115'